US006164409A

United States Patent [19]

Berger

[11] Patent Number: 6,164,409

[45] Date of Patent: Dec. 26, 2000

[54] WAX GUARD MEMBRANE FOR HEARING AIDS

[76] Inventor: Ralph Berger, 2 Underwood Cir., Lincoln, Mass. 01773

[21] Appl. No.: 09/209,741

[22] Filed: Dec. 11, 1998

[51] Int. Cl.[7] ........ A61B 7/02

[52] U.S. Cl. ........ 181/135; 181/130; 181/134; 381/322; 381/324; 381/325; 381/328; 128/864; 128/865; 128/867

[58] Field of Search ........ 181/129, 130, 181/135, 134; 381/322, 324, 325, 328; 128/864, 865, 867

[56] References Cited

U.S. PATENT DOCUMENTS

| | | | |
|---|---|---|---|
| 4,972,488 | 11/1990 | Weiss et al. | 381/325 |
| 4,987,597 | 1/1991 | Haertl | 381/325 |
| 5,278,360 | 1/1994 | Carbe et al. | 181/135 |
| 5,712,918 | 1/1998 | Yoest | 381/325 |
| 5,748,743 | 5/1998 | Weeks | 381/322 |

*Primary Examiner*—David Martin
*Assistant Examiner*—Khanh Dang

[57] ABSTRACT

A non porous wax guard for an in-the-canal hearing aid is in the form of a membrane or diaphragm which completely covers the mouth of the round or other shape outlet of the hearing aid. The membrane is made of plastic or metalized plastic, or stainless steel, having a diameter of between 0.20 inches and ⅜ inch, and a thickness of between 0.0005 inches and 0.001 inches. The membrane is affixed to the mouth of the sound outlet by a number of methods. It may be attached to a thin ring of plastic material, and attached with a spring clip to a recess in the sound outlet. It may simply be bonded, by adhesive or heat bonding, to the recess. It may be affixed to a cylindrical mount, and press-fit into the port. Or, as an alternative, the cylindrical mount may be threaded, and mated with an internal thread cut into the sound outlet. Although wax may build up externally on the membrane, it may be easily removed with a wipe of a tissue, whereas, without the wax guard, the sound outlet itself must be cleaned with an instrument or other device, risking damage to the hearing aid or requiring a hearing aid professional to do the cleaning.

12 Claims, 10 Drawing Sheets

Experimental Setup

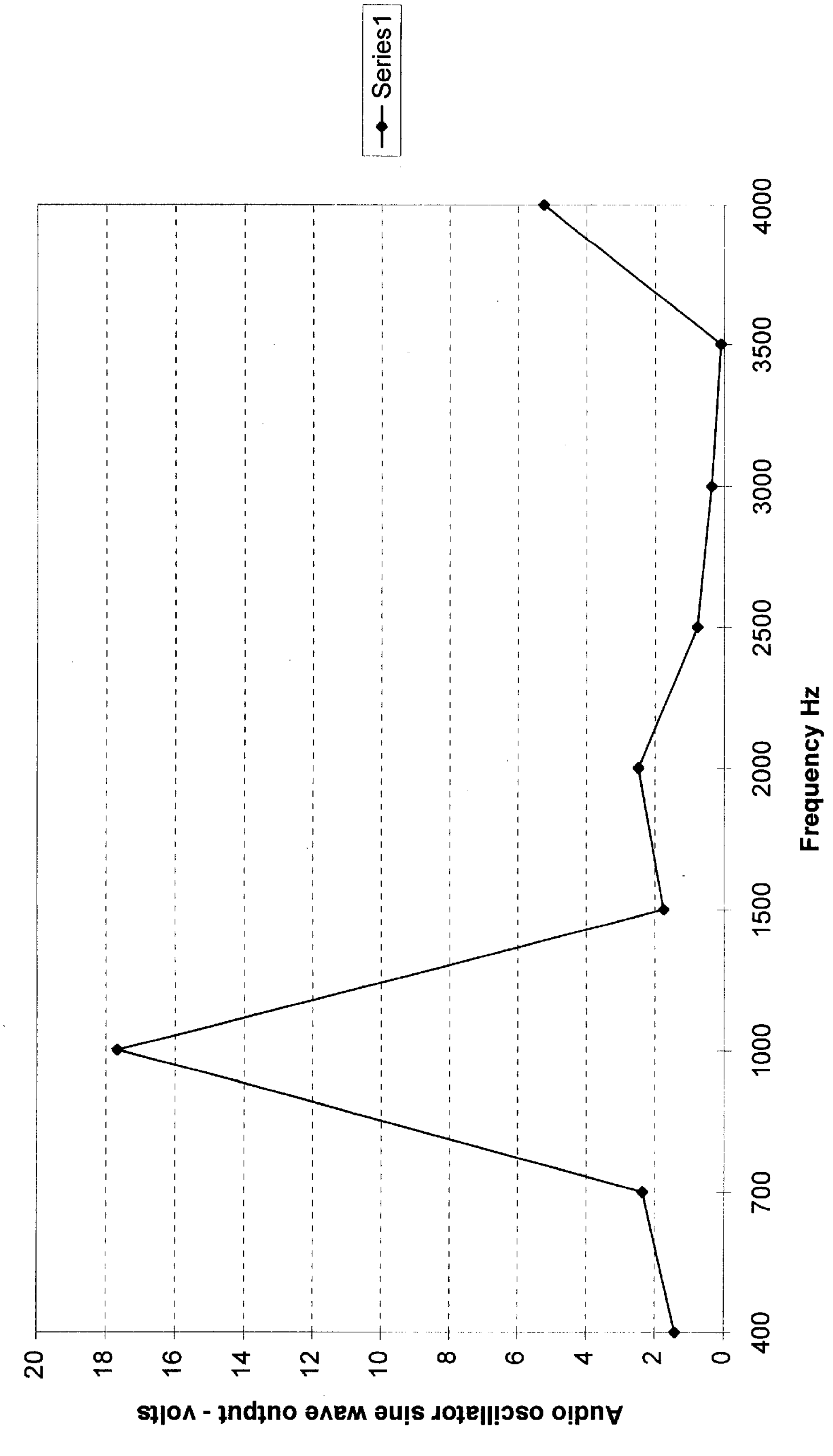
Fig. 4 Input voltage for 70dB output

Fig. 5 - Effect of Wax on Frequency Response
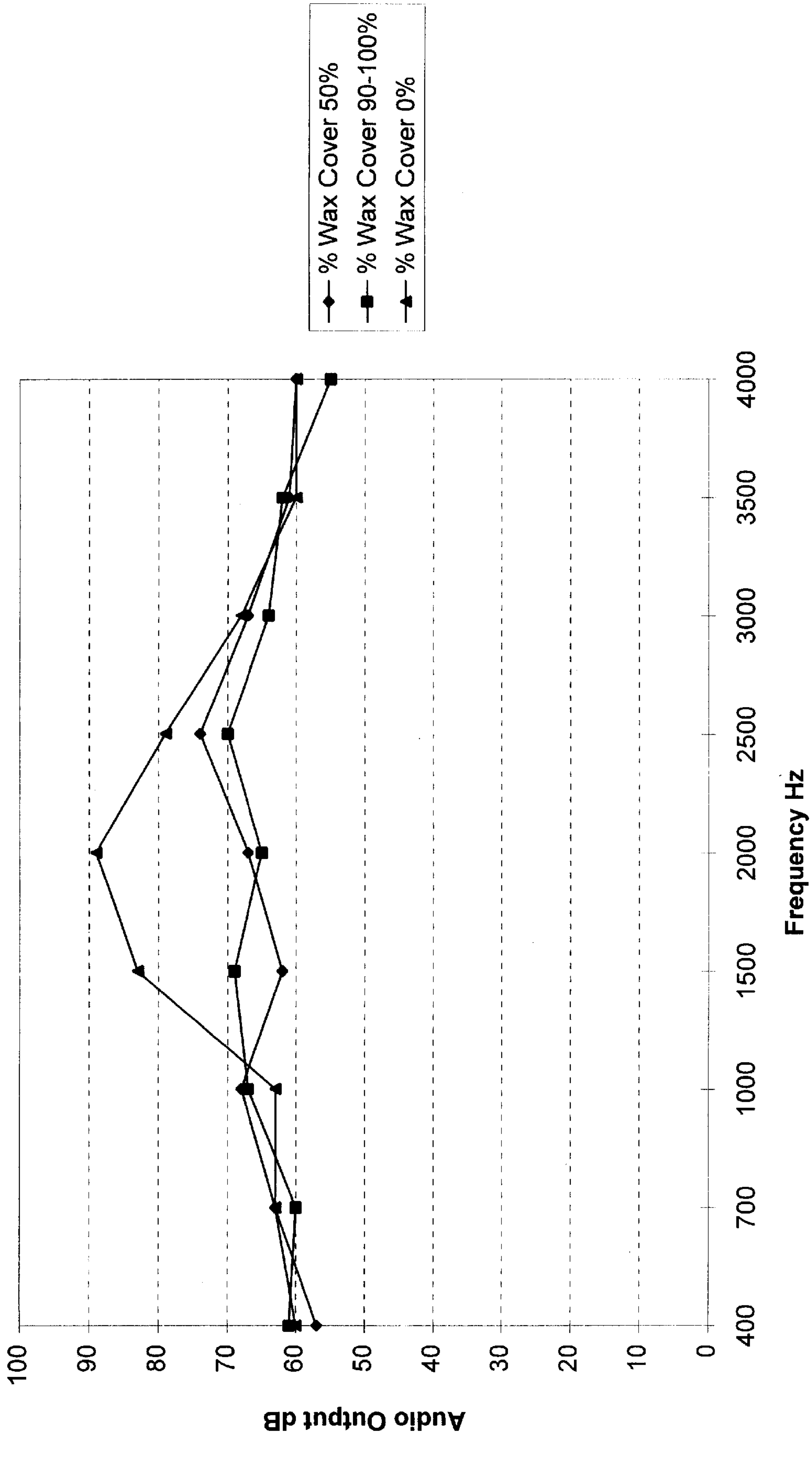

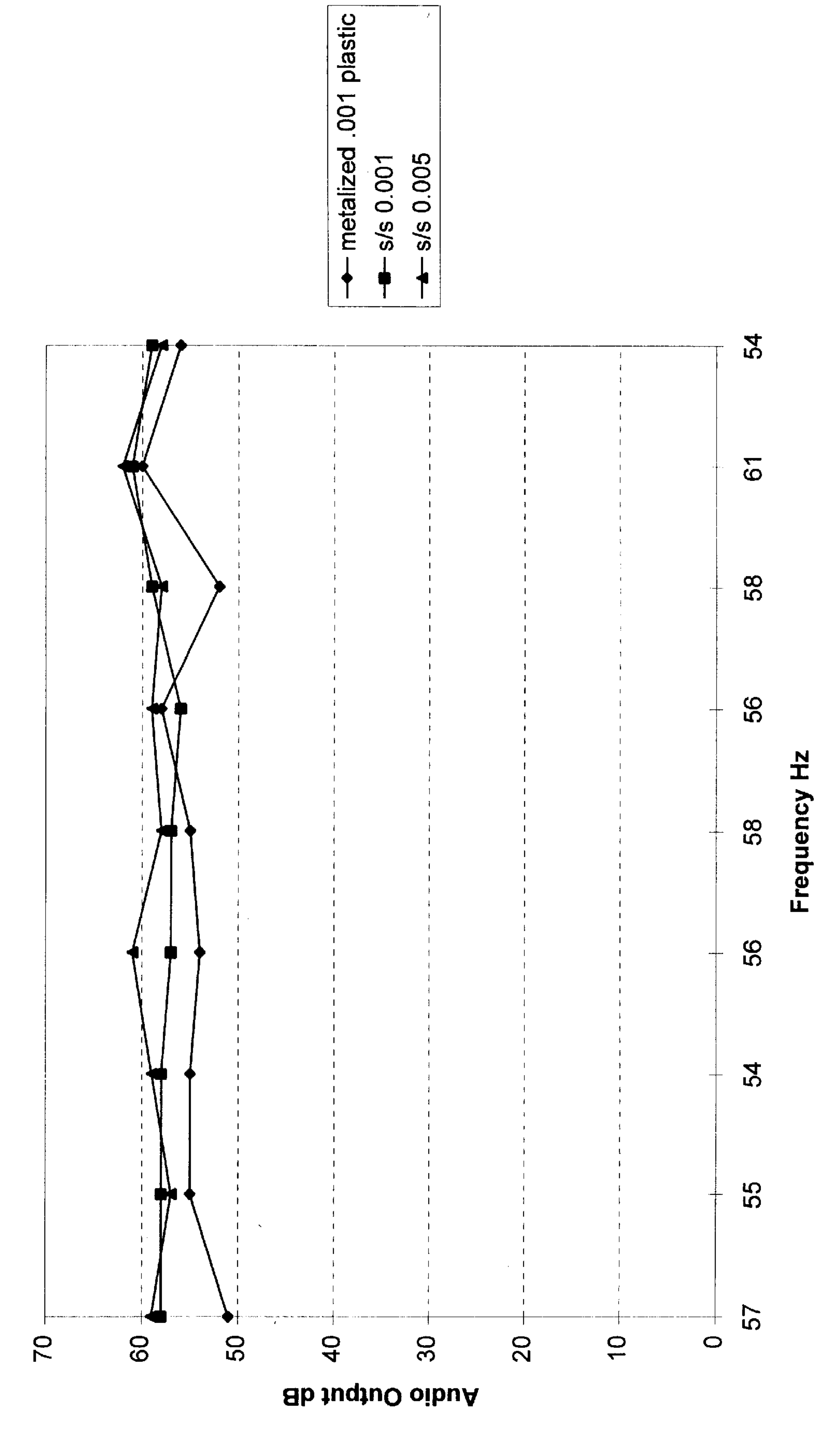
Fig. 6 - Frequency response for 0.20 inch diameter diaphrams

Fig. 7 - Frequency response for 0.40 inch diameter diaphrams
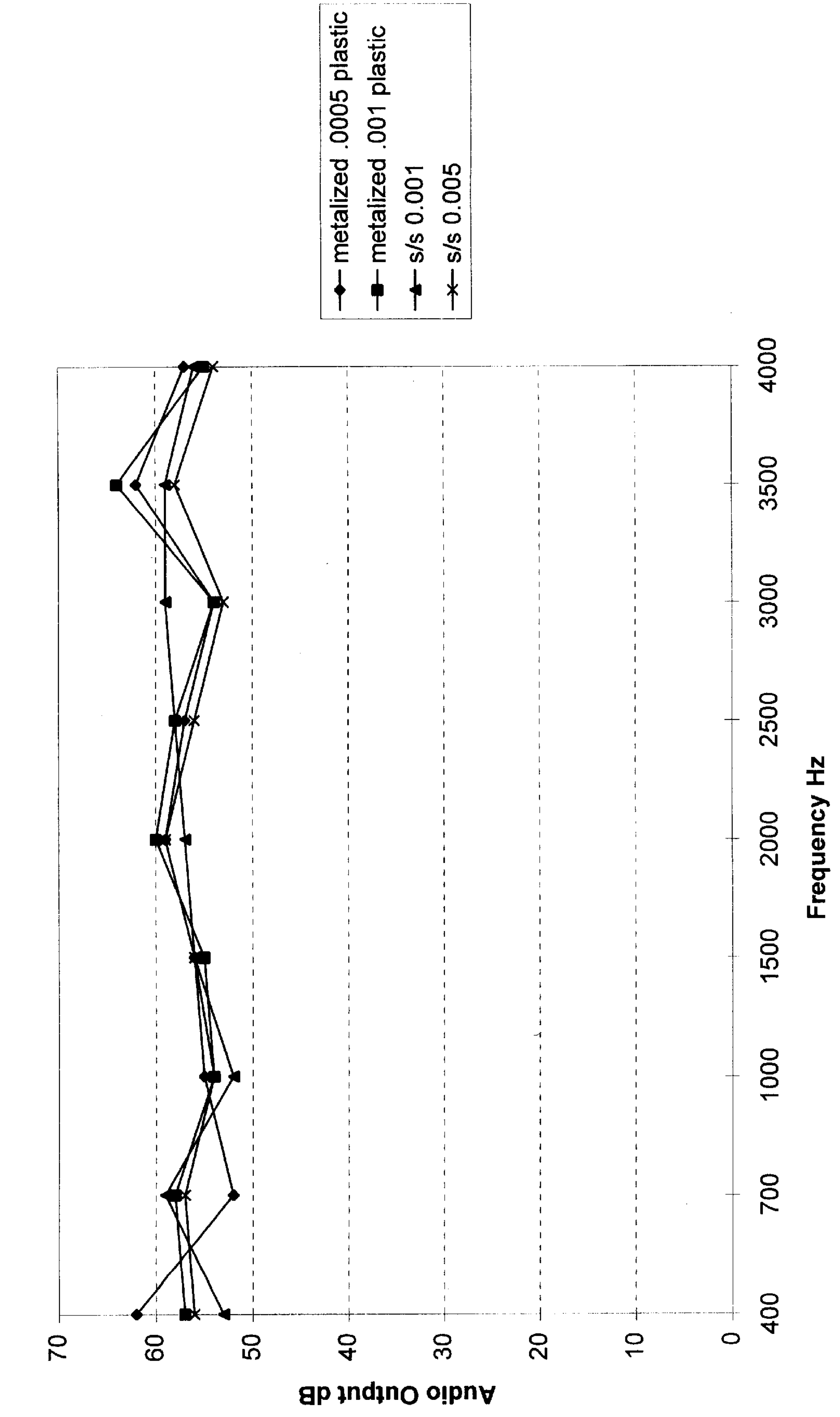

Fig. 8 - Frequency response for 3/8 inch diameter diaphrams
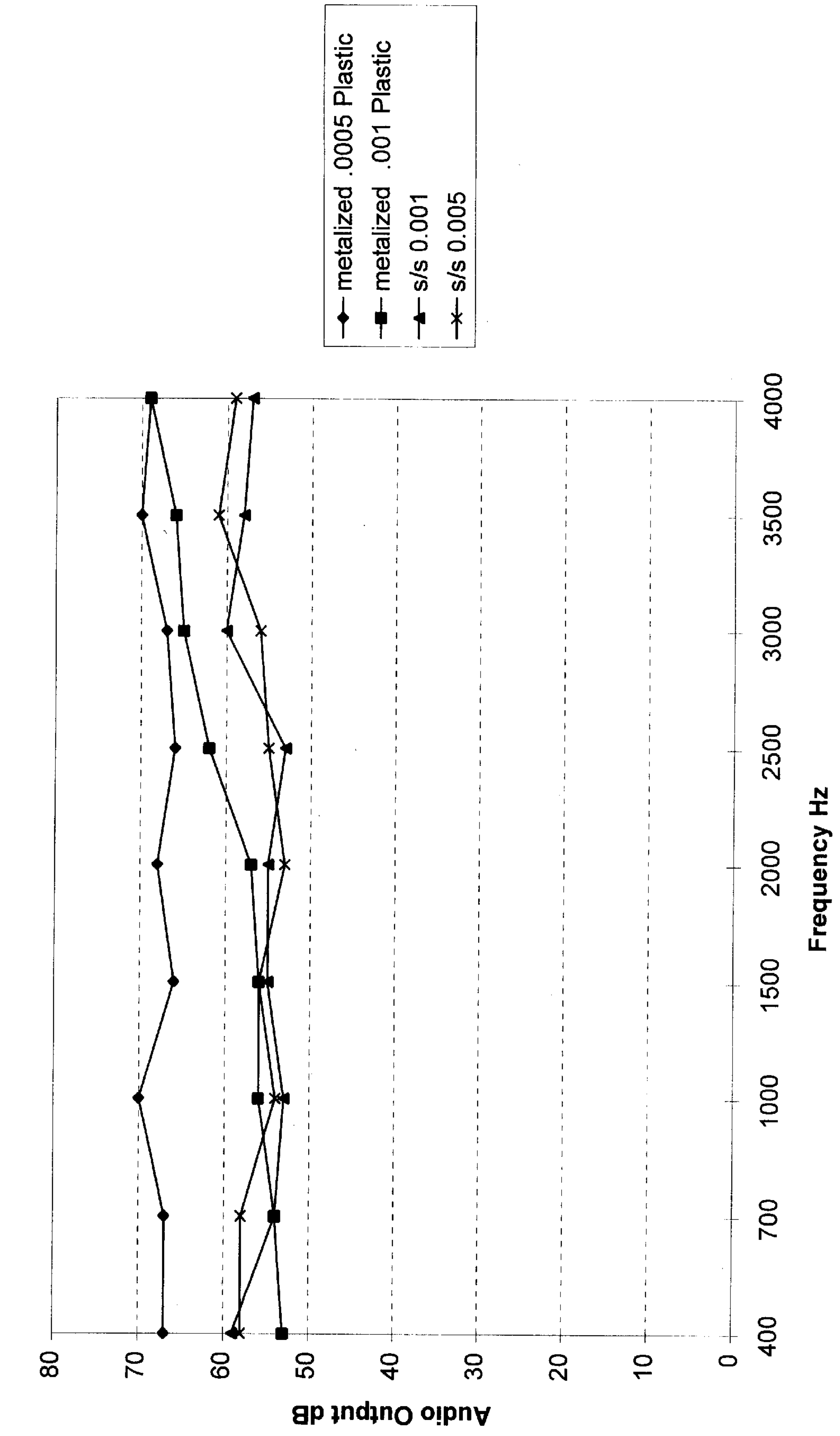

WAX GUARD MEMBRANE FOR HEARING AIDS

FIELD OF THE INVENTION

This invention relates to wax guards for hearing aids to prevent clogging of the speaker orifice with wax that is naturally produced in the ear canal.

BACKGROUND OF THE INVENTION

The current invention provides a means to prevent the buildup of wax in hearing aids from clogging the sound outlet, and preventing the sound from the hearing aid from reaching the eardrum of the wearer. Such wax buildup has effectively reduced the use of hearing aids which reside in the ear canal, where wax buildup occurs. As a result of such wax buildup, and the difficulty of cleaning, many users simply stop using their hearing aids.

The present invention provides a solution to the wax problem by covering the speaker orifice with a membrane, which vibrates as a result of sounds generated by the hearing aid and is located at the mouth of the speaker orifice, where accumulated surface wax can be simply wiped or safely brushed off.

Hearing aids for persons with impaired hearing are widely available, with millions of users world wide.

Hearing aids are available in a variety of types, including Custom In the Ear (ITE), In the Canal (ITC) and Completely in the Canal (CIC) instruments. Typically, all types are self-contained; with a miniature microphone, amplifier and transducer speaker inside the instrument carrying amplified sound directly to the ear canal and auditory system. Most hearing aids have an adjustable volume control and are powered by small, replaceable batteries.

The ITC, CIC, or other in-canal types are the subject of this invention. A typical instrument of this type is shown in FIGS. 2*a,* 2*b,* and 2*c* (prior art). Its body is an integrally formed plastic shell consisting generally of three parts: the base 30, midsection 31, and neck 32. When worn the neck is inserted into the ear canal, with the base exposed and visible when the ear is viewed by onlookers.

Within the body of the hearing aid is contained a battery compartment 24, a microphone 44 which receives sound to be amplified, an amplifier 46 whose input is connected to the microphone 44 by wiring (not shown) to amplify the sound picked up by the microphone 44, and a sound transducer 48, or loudspeaker to receive the amplified signal from the amplifier 46 and convert the signal into sound. The frequency characteristics of the hearing aid are generally tailored to approximately compensate for the hearing loss characteristics of the wearer.

The ambient sound enters the microphone through microphone orifice 26, located in the base 30, and the microphone output is amplified, shaped and converted via the speaker to an audio output. This sound is transmitted typically through a flexible tube 50 and through an sound outlet 42 in the neck 32, and thence into the user's ear. The sound outlet 42 is generally but not exclusively cylindrical in shape, with an area rather larger than the tube. The tube 50 is affixed to the shell at point 44 of the neck 32, and may also be affixed to the speaker 48, by adhesive means, heat bonding, or the like. Tube 50 protects speaker 48 during user handling and cleaning. Also present is a breather tube 52, which allows air to circulate within the hearing aid, and allow moisture to exit.

In use this construction has been problematic, due to the tendency of ear wax to cover and/or be inserted into the outlet port, thereby degrading the quality and level of the sound reaching the eardrum from the hearing aid, or, indeed, substantially reducing the intelligibility of the sound from reaching the eardrum so as not to be useful to the user.

The user needs some way to remove the wax, since the manufacturers of these devices do not normally provide a practical means for the generally elder user to do so. The user may receive a brush for this purpose, but the brush is difficult to use effectively, and may even push wax further into the orifice. The user must be careful not to damage the speaker. A number of inventions have attempted to solve this problem by placing baffles and barriers of various types in the sound outlet. These include U.S. Pat. No. D355,702 (Johnson), U.S. Pat. No. 5,278,360 (Carbe), U.S. Pat. No. 4,972,488 (Weiss), U.S. Pat. No. 4,870,689 (Weiss), and U.S. Pat. No. 4,553,627 (Gastmeier).

All of these barriers, however, can still allow some wax to enter, and further make it more difficult to remove wax, once it has appeared within the hearing aid.

The present invention, in contrast, provides an impermeable seal against the entry of wax. This invention is in the form of a membrane which vibrates in response to the sound produced by the hearing aid speaker and is located at the mouth of the exit port where it meets the exterior of the neck. Any wax which adheres to this smooth membrane may be easily wiped off by the user with a brush, cloth or tissue without damaging the speaker. And the membrane, if properly designed, causes little or no attenuation of the sound leaving the hearing aid and entering the ear canal, and further causes little or no distortion of the processed sound, maintaining its frequency characteristics to a high degree of fidelity.

SUMMARY OF THE INVENTION

It is an object of the present invention to provide a wax guard which will allow the user to avoid wax buildup that clogs the outlet of a ITC and CIC hearing aid, or to confine the wax buildup to an easily cleanable area. It is a further object to provide such a wax guard without impairing the quality or volume of the sound reaching the eardrum of the user.

According to one aspect of the invention, a wax guard for an in-channel hearing aid having a substantially small area sound outlet includes a membrane, of circular or other shape, entirely covering the sound outlet.

According to a second aspect of the invention the membrane is stainless steel having a thickness of between 0.005 and 0.001 inches, and having a diameter of between 0.20 and 0.375 inches.

According a third aspect of the invention, the membrane is metalized plastic having a thickness of between 0.005 and 0.0005 inches, and having a diameter of between 0.20 and 0.375 inches.

According to a fourth aspect of the invention, the guard further comprises a cylindrical mounting, the membrane stretched across the mouth of said mounting, so that the mounting may be pressed into the sound outlet.

According to a final aspect of the invention sound outlet has an internal female thread, and the mounting has a cooperating male external thread, so that the mounting may be screwed into the sound outlet.

BRIEF DESCRIPTION OF THE DRAWINGS

These, and further features of the invention, may be better understood with reference to the accompanying specification and drawings depicting the preferred embodiment, in which:

FIG. 4 depicts a plot of voltage vs. frequency for 70 db output for the test setup.

FIG. 5 depicts a plot of dB vs. frequency which demonstrates the effects of wax buildup on the invention before cleaning.

FIG. 6 depicts a plot of dB vs. frequency for 0.20 inch diameter membranes.

FIG. 7 depicts a plot of dB vs. frequency for 0.40 inch diameter membranes.

FIG. 8 depicts a plot of dB vs. frequency for ⅜ inch diameter membranes.

DESCRIPTION OF THE PREFERRED EMBODIMENTS

Testing of the Configurations

In order to determine the optimum membrane configuration for this invention, I first tested a number of membranes made of different materials, and having different thicknesses and diameters.

Figure 1:
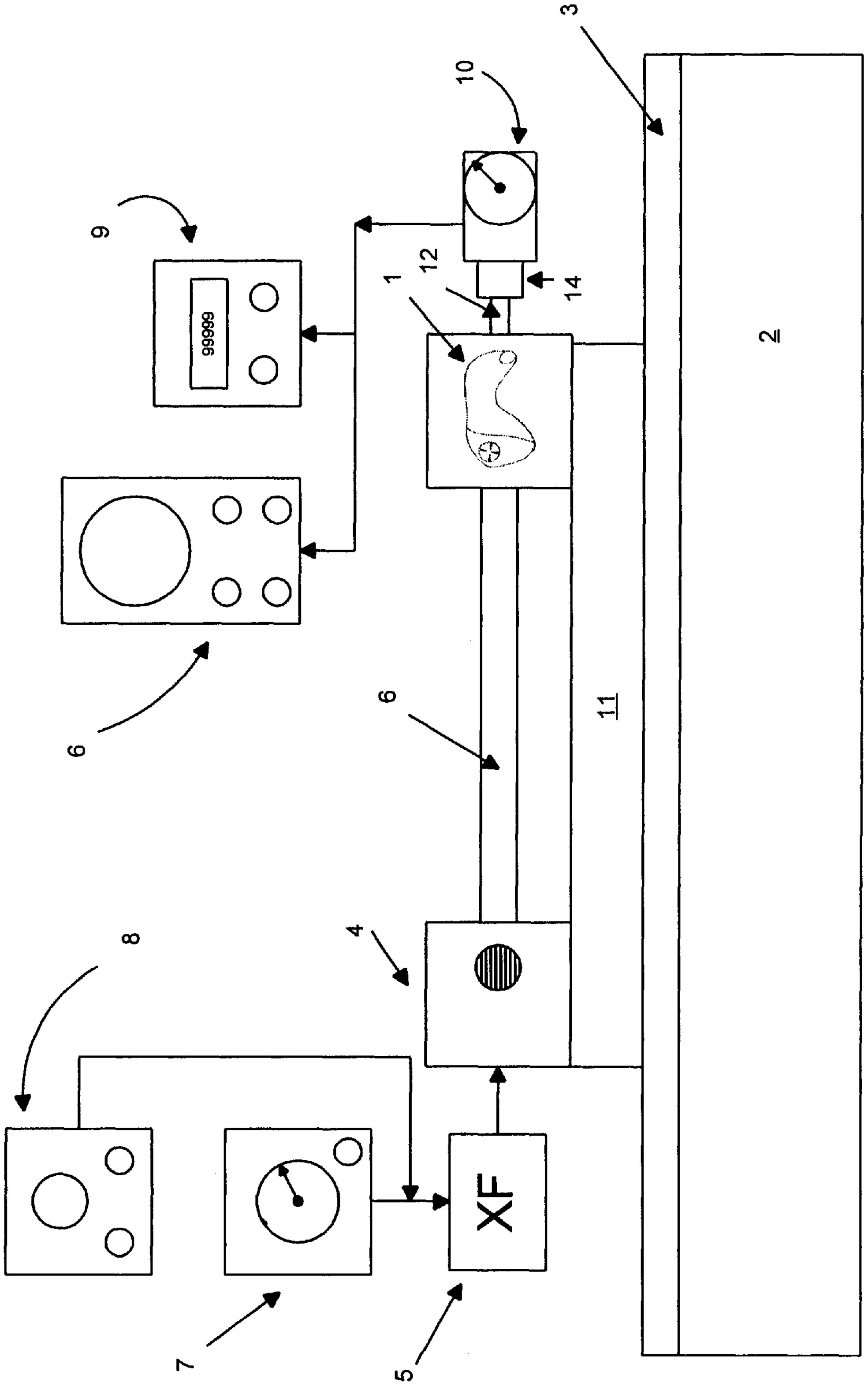
FIG. 1 depicts the experimental setup used to test various configurations of the invention.
Figure 2A:
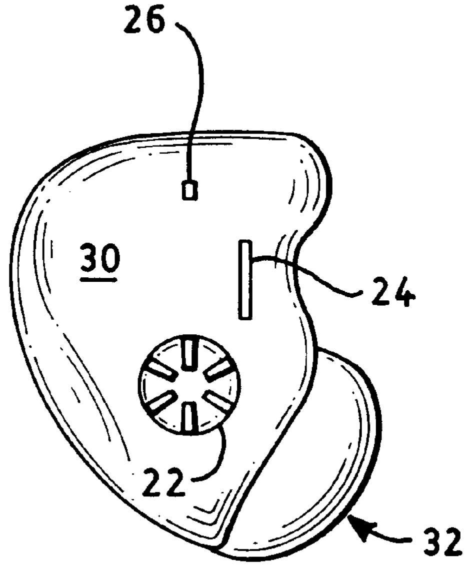
FIG. 2*a* depicts a perspective view of the hearing aid, as seen from the base.
Figure 2C:
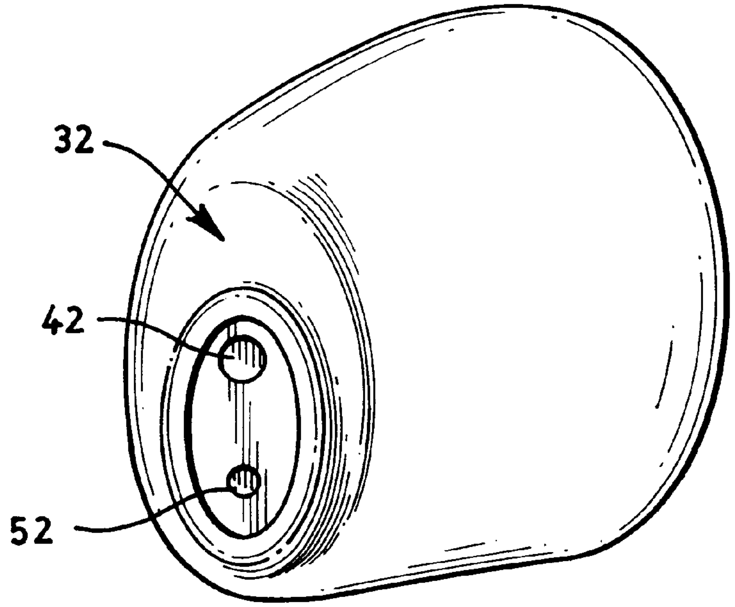
FIG. 2*c* depicts a perspective view of the hearing aid, as seen from the neck.
Figure 2B:
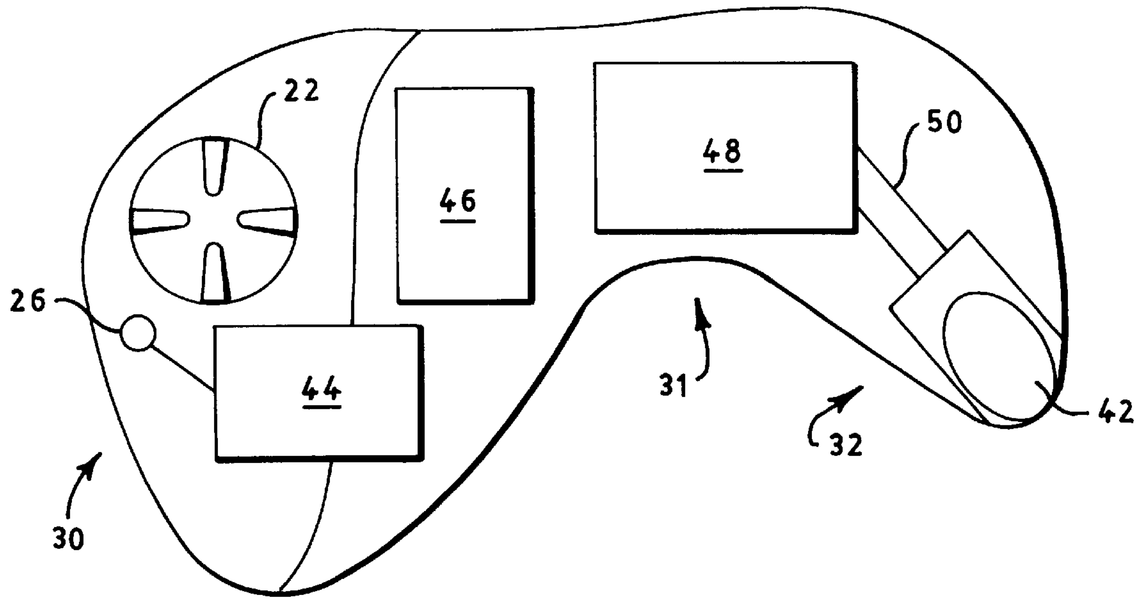
FIG. 2B PRIOR ART
FIG. 2*b* depicts a section view of the hearing aid.

The experimental set-up is shown in FIG. 1 to obtain repeatable adjustment. The setup used an Bausch and Lomb optical rack and pinion bench 11 set on a pool table 2 to provide a stable platform. A foam layer 3 was placed between the optical bench and the pool table to dampen ambient mechanical vibration, and substantially reduce transmission through the pool table.

One earphone 4, with the foam cover removed, made by Electro-static Dynamic Systems, +was used as the sound generator, driven by a Hewlett-Packard model 200AB audio oscillator 8 through a 70 volt, 8 ohm transformer (XF) 5. A Radio Shack model 22-185A digital multimeter 7 was used to monitor the AC voltage output of the audio oscillator.

The sound from the earphone 4 was transmitted through a closely coupled metal tube 6 to the base, or microphone input end of the hearing aid 1. The output, speaker end, or neck of the hearing aid 1, which normally is inserted in the ear canal of the user, was inserted into a plastic tube 12, and the sound from this tube is closely coupled to a metal tube 14 to be picked up by a Radio Shack model 33-2055 sound level meter 10, whose electrical output was connected to a Radio Shack model 22-174B digital multimeter 9, and also, in parallel, to a Tektronix dual-beam oscilloscope 6. The oscilloscope was used to visually check the output waveforms for distortion.

The setup was first tested without a hearing aid to calibrate in the test setup. Referring to FIG. 4, the audio oscillator voltage to the transformer was adjusted so that the sound level mmeter output measured 70 dB for each frequency tested. It can be seen, referring to FIG. 4, that the setup is not linear.

Next, a hearing aid was inserted into the setup, and the sound level meter output was measured for the same voltages which generated the 70 db outputs in FIG. 4. The frequency response of the user's hearing aid tested, an ITC model manufactured by Siemens, is not linear at the frequencies tested, between 400 and 4000 Hz, the output varying between 56 and 87 dB due to it's design for hearing loss compensation.

Next, the hearing aid was modified by inserting the wax guard membrane, a 0.0005 inch thick, metal coated polyvinyl manufactured by Precision Brand Products, Inc., of Downers Grove, Ill., and having a diameter equal to that of the hearing aid sound outlet. The membrane does not attenuate, but generally improve the shape of the frequency response of the hearing aid itself, particularly around 2000 Hz. A third test series, using a membrane of the same diameter as series 2, but made of stainless steel (also manufactured by Precision Brand Products), with a thickness of 0.001 inch, produced similar results, also showing an improved peak around 2000 Hz for smoother response.

Since the use of the hearing aid in the ear canal produces a wax buildup over time, the hearing aid with the current invention installed was worn to produce a wax buildup, and the effect of this buildup without cleaning was then tested. After about 30 hours of use, a buildup of approximately 20 mg of wax was observed. This amount corresponds to the 50% wax cover represented by Series 1 of FIG. 5. As seen by referring to FIG. 5, the response is attenuated by about 21 dB at about 2 kHz, and is substantial between 1500 kHz and 2500 kHz. This amount of attenuation in this part of the audio spectrum substantially impairs the utility of the hearing aid. However, it should be reiterated here, that with the current invention the wax may be removed by simply wiping the membrane with a cloth or tissue, or by use of a soft brush.

Further reference to FIG. 5 shows that the frequency response is further degraded when the 40 mg wax over the membrane is increased to 90–100%.

Referring next to FIGS. 6, 7, and 8, different membrane materials, of different diameters, were tested. The diameters of the membranes represented the diameter of material freely suspended, and allowed to vibrate. To test different diameters, it was necessary to enlarge the sound outlet accordingly. These tests didn't include the hearing aid.

As FIG. 6 shows, metalized plastic of 0.0005 inch and 0.001 inch diameters, and stainless steel of 0.001 inch and 0.005 inch diameters, produced very similar results, and are equally appropriate for use in the current invention.

Included in FIG. 6 is a calibrator plot of audio oscillator voltage v. dB output, representing the voltage required to produce the 70 dB output when the test setup was used without any hearing aid present.

FIG. 7 depicts the frequency response of the plastic and stainless steel membranes with a freely-suspended diameter of 0.040 inches. FIG. 7 displays the same general results as FIG. 6, showing no substantial attenuation over the range tested.

FIG. 8 depicts the frequency response of plastic and stainless steel membranes having a freely-suspended diameter of 0.375 inch. This diameter is the largest contemplated for the current invention, and even at these frequencies there is no substantial sine wave distortion. The 0.001 plastic membrane, which shows a gain of about 10 dB at 4000 Hz.

Figure 3A:
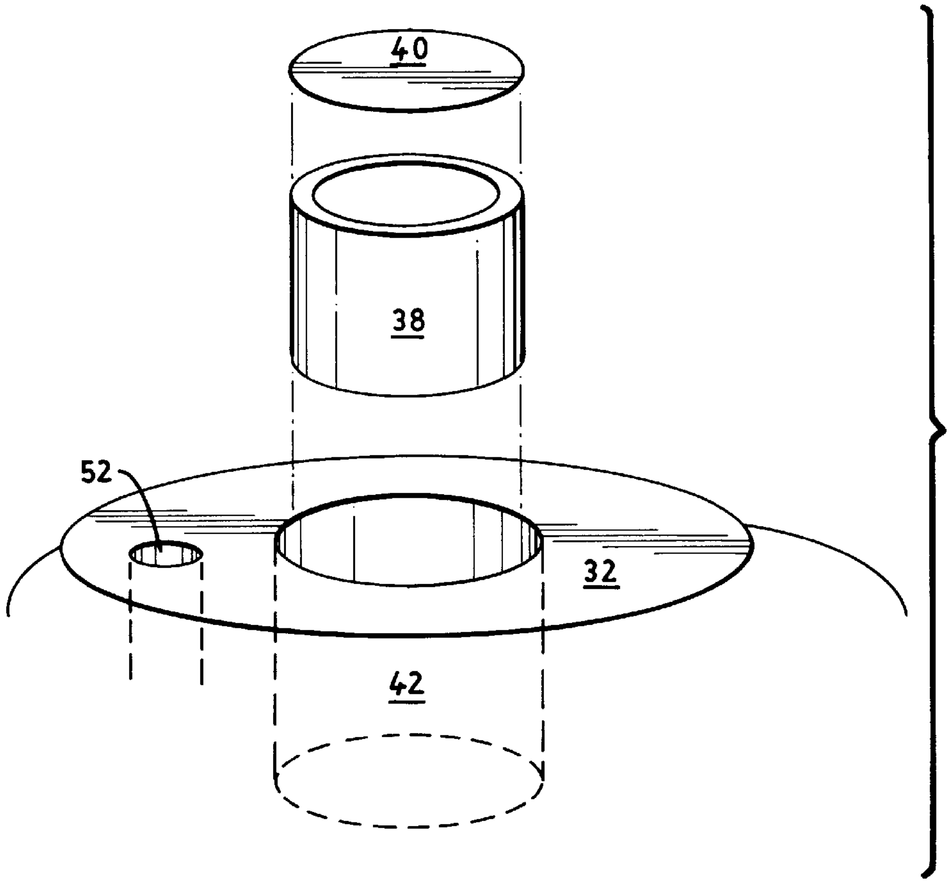
FIG. 3*a* depicts a perspective view of the guard having a membrane and a cylindrical mounting which press-fits into the sound outlet.

The invention may be understood by first referring to FIG. 3A, which depicts a non-porous membrane 40, attached to a cylindrical mounting 38, of approximately the same diameter or size as that of the sound outlet 42. Also depicted in FIG. 3A is a breather vent 52, which is normally found on the neck 32 of the hearing aid in proximity to the sound outlet.

Figure 3B:
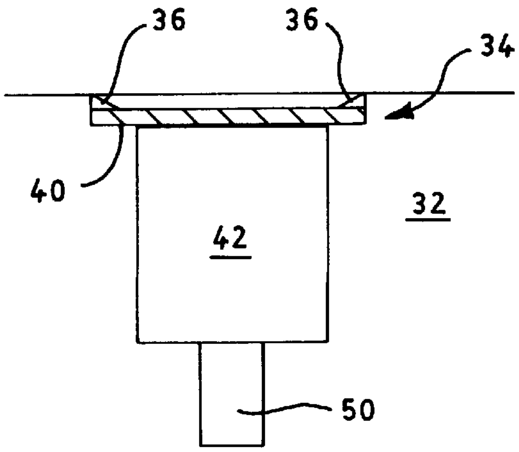
FIG. 3*b* depicts the guard bonded in a slight recess at the mouth of the sound outlet.
Figure 3C:
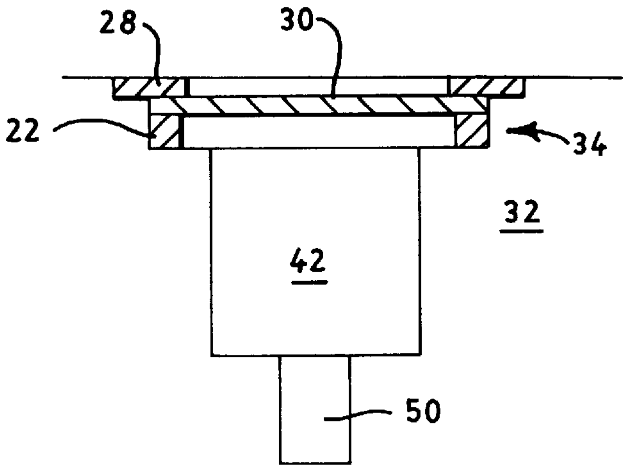
FIG. 3*c* depicts the guard having a spring clip retaining the membrane, bonded to a mounting ring, within a slight recess in the outlet port.
Figure 3D:
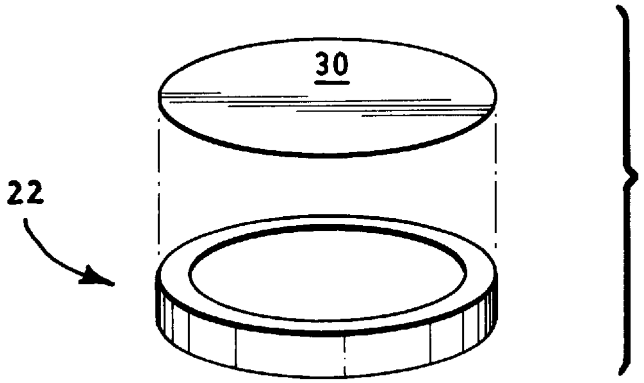
FIG. 3*d* depicts the guard having a spring clip retaining the membrane, bonded to a mounting ring, within a slight recess in the outlet port.
Figure 3E:
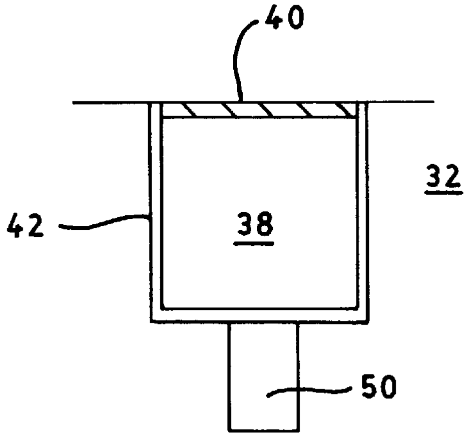
FIG. 3*e* depicts a section view of the guard of FIG. 3*a,* inserted almost flush with the hearing aid surface into the outlet port.

The mounting 38 in this embodiment makes a press-fit connection with the sound outlet, and when fully inserted, extends flush with the neck, as shown in FIG. 3*e*.

Although, intuitively, blocking the sound outlet would seem to prevent the sound produced by the hearing aid from reaching the wearer's ear drum, the experimental results shown in FIGS. 4 through 8 demonstrate that this is not the case. Ideally, a non-porous circular membrane with a diameter of 0.040 inch, and made from metalized plastic or stainless steel, of a thickness of between 0.0005 and 0.001 inches, will transmit the sound produced internally with minor gain or attenuation and have a smooth response.

A second preferred embodiment is depicted in FIG. 3B, wherein a circular recess 34, coaxial with the sound outlet 42, is milled into the neck 32 of the hearing aid, at the mouth of the outlet, where it meets the outer surface of the neck. In this embodiment, a non-porous membrane, of the same material and dimensions as the membrane of the first preferred embodiment, is bonded to the recess with adhesive bonding 36 at the edges of the membrane where it meets the recess.

A third preferred embodiment, in which the non-porous membrane is affixed by bonding methods to a mounting ring, is depicted in FIGS. 3C and 3D. In FIG. 3D, it is seen that the membrane 30 is affixed to the mounting ring 22 at the periphery of the membrane, forming an assembly with a rigid, circular edge. This assembly is then inserted into a recess 34, similar to that of the second preferred embodiment. The assembly formed by the membrane and ring is then retained by a spring clip 28 milled or otherwise formed into the edge of the recess.

Other means of securing the membrane are contemplated. The cylindrical mounting of the first preferred embodiment may be modified by forming an external screw thread in the mounting, and forming a mating, internal thread in the sound outlet, so that the mounting cylinder may be screwed into the sound outlet, and unscrewed for maintenance or replacement. If the proper type of thread is chosen, or if the sound outlet is slightly tapered, the mounting may be securely screwed into the outlet so that it does not come undone easily, without the wearer's wanting it removed.

It will be apparent that improvements and modifications may be made within the purview of the invention without departing from the scope of the invention defined in the appended claims.

I claim:

1. A non-porous wax guard for an in-the-ear-canal hearing aid having a speaker which generates a first sound wave and a sound outlet, the wax guard comprising a rigid, non-sound-permeable vibratable membrane entirely covering the outlet, wherein said membrane vibrates as a result of the first sound wave, resulting in a second sound wave in the ear canal similar in amplitude and frequency response to the first sound wave.

2. The wax guard of claim 1, wherein the membrane is chosen from the group consisting of:

stainless steel having a thickness of between 0.005 and 0.001 inches;

polyester of a thickness of between 0.01 and 0.0005 inches;

vinyl of a thickness of between 0.01 and 0.0005 inches;

metal-coated polyester of a thickness of between 0.01 and 0.0005 inches; and metal-coated vinyl of a thickness of between 0.01 and 0.0005 inches.

3. The guard of claim 2, wherein the diameter of the membrane is between 0.375 inch and 0.020 inches.

4. The guard of claim 3 wherein the guard further comprises a mounting, the membrane extended across the mouth of said mounting, so that the mounting may be pressed into the sound outlet to affix the guard thereto.

5. The guard of claim 4, wherein the membrane is substantially circular in shape, and the mounting is substantially cylindrical in shape.

6. The guard of claim 5, wherein the sound outlet has an internal thread formed therein, and the mounting has a mating external thread, so that the mounting may be screwed into the sound outlet.

7. A method for preventing wax from entering a sound outlet of an in-the-ear-canal hearing aid, having a speaker which generates a first sound wave, comprising:

forming a rigid, non porous, non-sound-permeable vibratable membrane;

forming a recess in the sound outlet; and bonding the membrane to the recess, thereby entirely covering the sound outlet, so that said membrane vibrates as a result of the first sound wave, resulting in a second sound wave in the ear canal similar in amplitude and frequency response to the first sound wave.

8. The method of claim 7, wherein the membrane is chosen from the group consisting of:

stainless steel having a thickness of between 0.005 and 0.001 inches;

polyester of a thickness of between 0.01 and 0.0005 inches;

vinyl of a thickness of between 0.01 and 0.0005 inches;

metal-coated polyester of a thickness of between 0.01 and 0.0005 inches; and metal-coated vinyl of a thickness of between 0.01 and 0.0005 inches.

9. A method for preventing wax from entering a sound outlet of an in-the-ear-canal hearing aid, having a speaker which generates a first sound wave, comprising:

forming a rigid, non porous, non-sound-permeable vibratable membrane;

forming a membrane assembly having a sound passage;

bonding the membrane to the membrane assembly;

forming a recess in the sound outlet; and affixing the membrane assembly in the recess by spring clip means, so that said membrane entirely covers the sound passage, and vibrates as a result of the first sound wave, resulting in a second sound wave in the ear canal similar in amplitude and frequency response to the first sound wave.

10. The method of claim 9, wherein the membrane is chosen from the group consisting of:

stainless steel having a thickness of between 0.005 and 0.001 inches;

polyester of a thickness of between 0.01 and 0.0005 inches;

vinyl of a thickness of between 0.01 and 0.0005 inches;

metal-coated polyester of a thickness of between 0.01 and 0.0005 inches; and metal-coated vinyl of a thickness of between 0.01 and 0.0005 inches, forming a membrane which covers the mouth of the sound outlet.

11. A method for preventing wax from entering a sound outlet of an in-the-ear-canal hearing aid, having a speaker which generates a first sound wave, comprising:

forming a rigid, non porous, non-sound-permeable vibratable membrane;

forming an internal thread in the sound outlet;

attaching the membrane to a substantially cylindrical mounting having a sound passage, the membrane entirely covering the sound passage, and the mounting having an external thread, mating to the sound outlet thread; and affixing the mounting in the sound outlet by screw-mating means, so that said membrane entirely covers the sound passage, and vibrates as a result of the first sound wave, resulting in a second sound wave in the ear canal similar in amplitude and frequency response to the first sound wave.

12. The method of claim 11, wherein the membrane is chosen from the group consisting of:

stainless steel having a thickness of between 0.005 and 0.001 inches;

polyester of a thickness of between 0.01 and 0.0005 inches;

vinyl of a thickness of between 0.01 and 0.0005 inches;

metal-coated polyester of a thickness of between 0.01 and 0.0005 inches; and metal-coated vinyl of a thickness of between 0.01 and 0.0005 inches.

* * * * *